United States Patent [19]

Strawn

[11] Patent Number: Plant 6,188

[45] Date of Patent: May 31, 1988

[54] MINIATURE ROSE PLANT NAMED FREE SPIRIT

[76] Inventor: Leslie E. Strawn, 10422 Morningside Ave., Garden Grove, Calif. 92643

[21] Appl. No.: 876,205

[22] Filed: Aug. 19, 1986

[51] Int. Cl.[4] ..... A01H 5/00

[52] U.S. Cl. ..... Plt./7

[58] Field of Search ..... Plt. 7

*Primary Examiner*—Robert E. Bagwill

[57] ABSTRACT

The subject of the present disclosure is a new and distinct variety of miniature rose plant characterized by salmon-coral buds and flowers of distinctive form and further indentified by the dwarf, upright, compact plant.

1 Drawing Sheet

1

The present invention relates to a new and distinct variety of hardy, bush type rose plant of the miniature class; the variety being primarily characterized — as to novelty — by the deep salmon buds and flowers which in general coloring effect are similar to Puerto Rico (Floribunda — U.S. Plant Pat. No. 3,519).

The variety is further characterized by:

An abundance of bloom, with flowers borne one to a stem with the occasional formation of two or three side buds.

Light sweet fragrance.

A plant which is vigorous, of upright, bushy growth habit, semi-glossy foliage with pointed leaflets; the buds and flowers being similar in form and size to Rise and Shine (miniature — U.S. Plant Pat. No. 4,231).

The plant, which has a normal height of 12 to 14 inches, can easily be maintained at a lesser height by occasional trimming.

A plant which grows and blooms satisfactorily both in a greenhouse or outdoors; is good for growing in pots; and provides excellent garden decoration as well as cut flowers.

The present variety of miniature rose was originated by me in my home greenhouse, located at Garden Grove, Orange County, Calif., under conditions of carefully controlled observation, as a cross between Prominent (Grandiflora — U.S. Plant Pat. No. 3,380) as the seed parent and Gold Pin (Miniature — non-patented) as the pollen parent.

Subsequent to origination of the variety I successfully asexualy reproduced it in my garden, located as foresaid, (Also propagated by Pixie Treasures Rose Nursery, 4121 Prospect Ave., Yorba Linda, Orange County, Calif.) by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate indentifications being by reference to The British Colour Council Horticultural Colour Chart, except where common terms of color definition are employed.

Type: Hardy; dwarf; bushy; upright; seedling; greenhouse; outdoors; cut flowers; garden decoration; pot plant.

Class: Miniature.

*Variety name.*—Free Spirit.

2

*Generic name.*—Pixiree.

Flowers borne: Singly on upright slender stems; occasional sidebuds.

Quantity of bloom: Abundant, both outdoors and in the greenhouse.

Bud:

*Peduncle.*—Straight; 4½ to 5 cm length; slender, sturdy, green or bronze; few glands, few hairs; few soft thorns.

*Size.*—Before calyx breaks — 2 to 2½ cm length.

*Form.*—Pointed; foliaceous parts extend beyond tip of bud one half or more of its length.

*Color.*—Medium green. As calyx breaks — color of outside petal showing new Nasturtium orange 6 10/2.

Bloom:

*Size.*—When fully open — small — averaging 4½ to 5 cm.

*Petalage.*—Double; 25 to 30 petals; arranged symmetrically.

*Form.*—Pointed, exhibition type. As the petals unfurl they remain in their upright position with the top edges flaring outward at the sides usually forming a point. The sepals remain upward through the three-quarter stage of bloom.

Petals:

*Substance.*—Moderately thick and of good substance.

*Texture.*—Smooth and satiny on both surfaces. Slightly veined.

*Shape.*—Outside petals: Broad with small point at apex. Pointed base. Intermediate petals: Same as outside petals. Inside petals: Same as intermediate petals but not as wide. Petaloids: Few, close to stamens.

Color: One half to three-quarters open flowers from plants grown outdoors at Pixie Treasures Rose Nursery, Yorba Linda, Calif. April 1986.

*Outside Petal.*—Outside surface: Close to Nasturtium orange 6 10/2 becoming slightly lighter toward the outer edges. Base color of light yellow blends upward into the center area. Inside surface: Close to Marigold orange 11/2 becoming slightly lighter toward the outer edges. Light yellow base.

*Intermediate petal.*—Outside surface: Same as outside petal. Same base. Inside surface: Same as outside petal. Same base.

*Inside petal.*—Same as outside and intermediate petals. Same base.

General color effect:

*Newly open flowers.*—Symmetrically arranged petals of Marigold orange with the lighter tones of Nasturtium orange of the outside surfaces giving a moderate two-tone effect. The light yellow base color being evident through the half open stage.

*Three to four days open.*—Keeps symmetry fully open with stamens showing. Color changes to a hue near Marigold orange 11/3 from exposure to sunlight.

Behavior: Opens well in all weather. Petal tend to hang on for 5 to 6 days then fall; calyx remains and occasionally forms a hip.

*Flower longevity* (April 1986).—Plant in pot — 3 to 4 days; plant in ground — 4 to 5 days; cut flowers at living room temperature — 3 to 4 days.

Reproductive organs:

*Stamens.*—30 to 35.

*Filaments.*—Uneven lengths — 3 to 4 mm; light yellow in color.

*Anthers.*—Golden; introse.

*Pollen.*—Moderate amount.

*Pistils.*—Project above disc.

*Styles.*—many; loosely bunched; uneven lengths — 2 to 3 mm; brown in color.

*Ovaries.*—Enclosed in calyx.

*Hips.*—Occasionally formed from self pollination.

*Sepals.*—Permanent; narrow, spear shaped.

*Seeds.*—Few if any.

Foliage:

*Leaves.*—Compound of five leaflets; length 6 to 8 cm; semi-glossy; occasionally seven leaflets.

*Rachis.*—Length 4 to 5 cm; upper side grooved; under side thornless or a few soft thorns.

*Stipules.*—Smooth; short with slender pointed auricles, flairing outward at approx. 45 degrees.

*Color.*—Medium green; rachis and serrated edges of leaflets usually bronze.

Growth:

*Habit.*—Dwarf; upright and rounded; height — 30 to 35 cm or 12 to 14 in.

*Growth.*—Vigorous; length between internodes — 3 to 4 cm; much branched.

*Canes.*—Slender and sturdy.

*Main stems.*—Dark green.

*Branches.*—Medium green; new branches — reddish green; much branched.

*Thorns.*—4 to 5 mm length; needle declining; dilated at base; sparsely thorned, some branches may be completely thornless.

*New shoots.*—Reddish or bronze tinted.

The following is claimed:

1. A new and distinct variety of miniature rose plant, hardy, dwarf, bushy, upright, rounded, much branched habit, substantially as illustrated and described; characterized by buds and flowers which are in a color hue similar to Puerto Rico (Floribunda — U.S. Plant Pat. No. 3,519) and giving the coloring effect of deep salmon; and resembling Rise and Shine (Miniature — U.S. Plant Pat. No. 4,231) in form and size, having buds and flowers of a distinct and unusual appearance as compared to other miniature rose plants; said flowers being fully double, unique in its exhibition form and further characterized by its vigor, abundance of bloom and foliage and ease of propagation from soft wood cuttings and by budding.

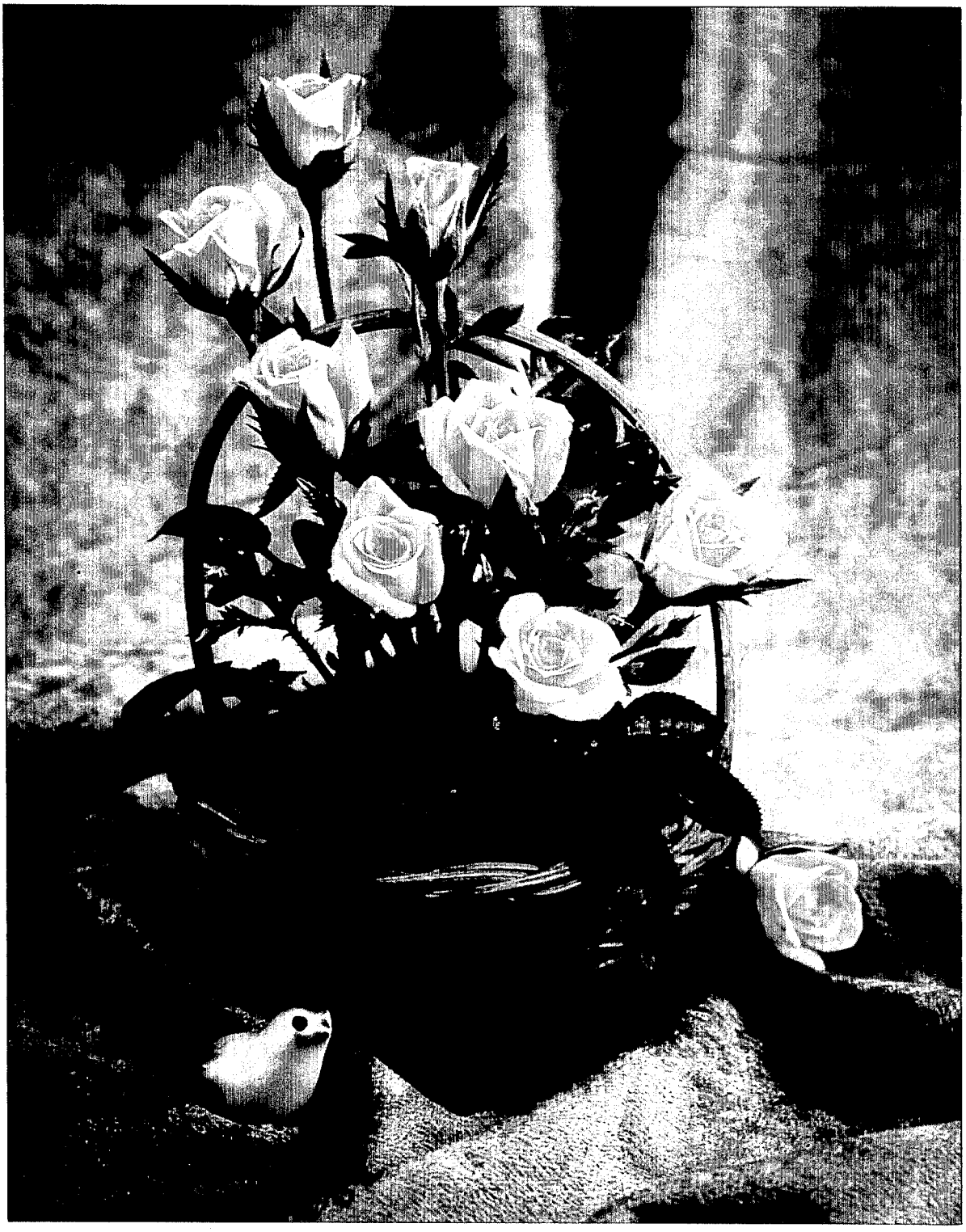

* * * * *